United States Patent [19]
Ishiguri et al.

[11] Patent Number: 4,618,620
[45] Date of Patent: Oct. 21, 1986

[54] FUNGICIDAL COMPOSITION

[75] Inventors: Yukio Ishiguri; Hirotaka Takano, both of Takarazuka; Yuji Funaki, Toyonaka, all of Japan

[73] Assignee: Sumitomo Chemical Company, Limited, Osaka, Japan

[21] Appl. No.: 765,574

[22] Filed: Aug. 14, 1985

Related U.S. Application Data

[63] Continuation of Ser. No. 484,957, Apr. 14, 1983, abandoned.

[30] Foreign Application Priority Data

Apr. 22, 1982 [JP] Japan ................................. 57-68097

[51] Int. Cl.$^4$ ...................... A01N 43/52; A01N 43/64
[52] U.S. Cl. ...................................... 514/383; 514/388
[58] Field of Search ................................ 514/383, 388

[56] References Cited

U.S. PATENT DOCUMENTS 4,285,722  8/1981  Worthington et al. ............. 424/269
4,331,675  5/1982  Regel et al. ........................ 424/269
4,435,203  3/1984  Funaki et al. ...................... 424/269

FOREIGN PATENT DOCUMENTS 2332207   6/1977  France .
2046260  11/1980  United Kingdom .

OTHER PUBLICATIONS

The Pesticide Manual, 6th Edition, pp. 32, 80, 288, 509, 517 and 518, (1979).
Systematic Fungicides, pp. 64–67, 78–81, (1972).

Primary Examiner—Allen J. Robinson
Attorney, Agent, or Firm—Stevens, Davis, Miller & Mosher

[57] ABSTRACT

A fungicidal composition which comprises an inert carrier and as an active ingredient (E)-1-(2,4-dichlorophenyl)-4,4-dimethyl-2-(1,2,4-triazol-1-yl)-1-penten-3-ol and a benzimidazole-thiophanate type fungicide in the ratio of 1 to 0.1 to 10 by part by weight in a total amount of 0.1 to 99.9% by weight.

2 Claims, No Drawings

FUNGICIDAL COMPOSITION

This application is a continuation of application Ser. No. 484,957 filed Apr. 14, 1983, now abandoned.

The present invention relates to a fungicidal composition which comprises, as an active ingredient, (E)-1-(2,4-dichlorophenyl)-4,4-dimethyl-2-(1,2,4-triazol-1-yl)-1-penten-3-ol (hereinafter referred to as Compound A) and methyl-1-(butylcarbamoyl)benzimidazol-2-yl carbamate (hereinafter referred to as Benomyl), 2-(4-thiazolyl)-benzimidazole (hereinafter referred to as Thiabendazole), methylbenzimidazol-2-yl carbamate (hereinafter referred to as Carbendazim), 2-(2-furyl)benzimidazole (hereinafter referred to as Fuberidazole), 1,2-bis(3-methoxycarbonyl-2-thioureido)benzene (hereinafter referred to as methyl thiophanate) or 1,2-bis(3-ethoxycarbonyl-2-thioureido)benzene (hereinafter referred to as thiophanate) which is benzimidazolethiophanate type fungicide, and an inert carrier.

As described in The Pesticide Manual, 6th Edition, the benzimidazole-thiophanate type fungicides are excellent chemicals as having both preventive effect and curative effect on a wide range of plant diseases of the fruit trees, vegetables and the like and having rapid effectiveness, remaining effectiveness as well as infiltration ability.

However, recently drug-resistant organisms appeared in the important plant diseases such as Powdery mildew, Gray mold and the like, presenting serious problems. (Longman: Systemic fungicides edited by R. W. March, 1972).

As mentioned in the UK Patent Application GB 2046260A, the Compound A is an excellent chemical having sufficient controlling effect on Powdery mildew, Rust and the like of cereals, fruit trees, vegetables and the like. In addition, the Compound A has excellent properties as exemplified by having a controlling effect on the resistant strain to benzimidazole-thiophanate type fungicides.

The present inventors have studied extensively on the fungicides which are able to control many plant diseases in an amount as small as possible and moreover at the same time. As the result, it was found that the composition of this invention is able to not only maintain the controlling effect of the ingredient compound, but also control many plant diseases both preventively and curatively in a small amount and at the same time.

The composition of this invention contains the Compound A and benzimidazole-thiophanate type fungicides as an active ingredient. The weight ratio of the two components is 0.1 to 10 parts by weight, preferably 0.5 to 5 parts by weight of benzimidazole-thiophanate type fungicide per 1 part by weight of the Compound A.

The pathogens on which the composition of this invention has controlling effect preventively or curatively are *Pyricularia oryzae, Cochliobolus miyabeanus, Rhizoctonia solani* of rice plant; *Erysphe graminis* f. sp. *hordei*, f. sp. *tritici*, *Gibberella zeae, Puccinia striiformis, P. graminis, P. recondita, P. hordei, Typhula sp., Micronectriella nivalis, Ustilago tritici, U. nuda, Pseudocercosporella herpotrichoides, Rhynchosporium secalis, Septoria tritici, Leptosphaeria nodorum* of barley; *Diaporthe citri, Elsinoe fawcetti, Penicillium digitatum, P. italicum* of citrus fruits; *Sclerotinia mali, Valsa mali, Podosphaera leucotricha, Alternaria mali, Venturia inaequalis* of an apple; *Venturia nashicola, Alternaria kikuchiana, Gymnosporagium haraeanum* of a pear; *Sclerotinia cinerea, Cladosporium carpophilum, Phomopsis sp.* of a peach; *Elsinoe ampelina, Glomerella cingulata, Uncinula necator, Phakopsora ampelopsidis* of a grape; *Gloeosporium kaki, Cercospora kaki, Mycosphaerella nawae* of a persimmon; *Colletotrichum lagenarium, Sphaerotheca fuliginea, Mycosphaerella melonis* of a melon; *Alternaria solani, Cladosporium fulvum* of a tomato; *Phomopsis vexans, Erysiphe cichoracearum* of an eggplant; *Alternaria japonica, Cercosporella brassicae* of Cruciferae vegetables; *Puccinia allii* of a spring onion; *Cercospora kikuchii, Elsinoe glycines, Diaporthe phaseolorum var. sojae* of a soy bean; *colletotrichum lindemuthianum* of a kidney bean; *Mycosphaerella personatum, Cercospora arachidicola* of a peanut; *Erysiphe pisi* of a pea; *Alternaria solani* of a potato; *Sphaerotheca humuli* of a strawberry; *Exobasidium reticulatum, Elsinoe leucospila* of a tea; *Alternaria longipes, Erysiphe cichoracearum, Colletotrichum tabacum* of a tobacco plant; *Cercospora beticola* of a sugar beet; *Diplocarpon rosae, Sphaerotheca pannosa* of a rose; *Septoria chrysanthemi-indici, Puccinia horiana* of a chrysanthemum; *Botrytis cinerea, Sclerotinia sclerotiorum* of a variety of crops and the like.

Consequently, the composition of this invention can be applied as a fungicide onto the paddy field, field, orchard, tea field, meadow, lawn field and the like.

In the actual use of the composition of this invention, only the ingredient compound may be applied without addition of any other components, but usually it is admixed with solid carriers, liquid carriers, surface active agents, and other formulating auxiliaries and formulated in the form of wettable powder, flowable, granular, dust and the like.

These compositions contain the active ingredients in an amount of 0.1 to 99.9%, preferably 1 to 99% by weight.

Examples of solid carriers include fine powder or granular of kaolin clay, attapulgite, bentonite, Japanese acid clay, pyrofilite talc, diatomaceous earth, calcite, corn stalk powder, walnut shell powder, urea, ammonium sulfate, synthesized silicone oxide hydrate, and the like. Examples of the liquid carriers include aromatic hydrocarbons, such as xylene, methylnaphthalene and the like; alcohols such as isopropanol, ethylene glycol, cellosolve and the like; ketones such as acetone, cyclohexanone, isophorone and the like; plant oil such as soy bean oil, cotton seed oil and the like; dimethylsulfoxide, acetonitrile, water and the like.

Examples of the surface active agents employed for emulsification, dispersion, wetting-spread and the like include anionic surface active agents such as alkyl sulfate ester salt, alkyl (aryl) sulfonate salt, dialkylsulfosuccinate salt, polyoxyethylene alkyl aryl ether phosphate salt, naphthalene sulfonic acid-formalin condensate and the like; non-ionic surface active agents such as polyoxyethylene alkyl ether, polyoxyethylene polyoxypropylene block copolymer, sorbitan fatty acid ester, polyoxyethylene sorbitan fatty acid ester and the like. Examples of the formulating auxiliaries include lignine sulfonate salt, arginate salt, polyvinyl alcohol, gum arabic, CMC (carboxymethylcellulose), PAP (isopropyl acid phosphate) and the like.

Formulation Examples will be shown hereinbelow. Parts are shown by parts by weight.

FORMULATION EXAMPLE 1

10 Parts of the Compound A, 20 parts of carbendazim, 3 parts of calcium lignin sulfonate, 2 parts of sodium lauryl sulfate and 65 parts of synthesized silicone oxide hydrate were pulverized well and admixed with one another to obtain a wettable powder.

FORMULATION EXAMPLE 2

1 Part of the Compound A, 2 parts of venomyl, 1 part of synthesized silicone oxide hydrate, 2 parts of calcium lignin sulfonate, 30 parts of bentonite, and 64 parts of kaolin clay were pulverized well and admixed with one another and kneaded with addition of water and then subjected to granulation and drying to yield granulars.

FORMULATION EXAMPLE 3

10 Parts of the Compound A, 15 parts of methyl thiophanate, 3 parts of polyoxyethylenesorbiton monooleate, 3 parts of CMC, and 69 parts of water were blended and pulverized by the wet method to the particle size of the active ingredient of 5 microns or less to yield a flowable.

FORMULATION EXAMPLE 4

0.5 Part of the Compound A, 1.5 parts of thiabendazole, 88 parts of kaolin clay and 10 parts of talc were pulverized and blended well to yield a dust.

These compositions are applied as such or after dilution with water onto the leaves and onto the soils to admix therewith. Increase in the controlling effect can be expected by the combination with other fungicides. Furthermore, these compositions may be used in combination with insecticides, acaricides, nematocides, herbicides, plant growth regulators, fertilizers, soil improving agents and the like.

In the practical use of the present composition, the amount of the active ingredient applied is usually 1 to 500 g, preferably 10 to 100 g per one are. In the dilution of the wettable powder, flowable and the like with water, the concentration of the active ingredients applied is 0.001 to 0.5%, preferably 0.01 to 0.1% and the above compositions can be applied as such without being added with granular and dust.

Control effect of the present composition on the plant disease is shown by the Test Examples. The tested compounds are the above said Compound A, Benomyl, Thiabendazol, Carbendazim, Fuberydazole, Methyl thiophanate, and Thiophanate. The fungicides used as a comparison reference are shown by the compound marks of the following table.

TABLE

| Compound mark | Chemical structure | Common name |
| --- | --- | --- |
| B | O‖Me$_2$N.S.N.S.CCl$_2$F‖O— phenyl | Dichlorofluanid |
| C | CN, Cl, Cl, Cl, Cl, CN (tetrachloroisophthalonitrile) | Chlorothalonil |

The control effect was evaluated by the numerical 6 steps and expressed by 0 to 5, depending on the disease conditions of the test plant, that is, colony and lesion of the leaves and stems.

5:No colony and lesion is observed completely.
4:About 10% of the colony and lesion is observed.
3:About 30% of the colony and lesion is observed.
2:About 50% of the colony and lesion is observed.
1:About 70% of the colony and lesion is observed.
0:There is no difference in disease condition rom the non-treatment.

TEST EXAMPLE 1

Control effect test on Gray mold of cucumber
(Preventive effect)

Sandy soil was packed in a plastic pot and cucumber (SAGAMI HANGJIRO) was sowed and the resulting seedling was grown in a greenhouse for 8 days. The wettable powder of the test compound formulated according to Formulation Example 1 was diluted with water to a predetermined concentration and sprayed onto the seedling of the cucumber which had developed cotyledons. After sprayed, an agar piece containing organisms causing Gray mold of cucumber was attached to the seedling of cucumber for inoculation. After inoculation, the seedling of cucumber was placed at 20° C. for 3 days in high humidity and the control effect was examined. The results were shown in Table 1.

TABLE 1

| Test compound | Concentration of active ingredient applied (ppm) | Control effect |
| --- | --- | --- |
| A | 10 | 0 |
| A | 3 | 0 |
| Benomyl | 10 | 3 |
| Benomyl | 7 | 3 |
| Thiabendazole | 10 | 2 |
| Thiabendazole | 7 | 2 |
| Carbendazim | 10 | 3 |
| Carbendazim | 7 | 3 |
| Fuberidazole | 10 | 2 |
| Fuberidazole | 7 | 2 |
| Methyl thiophanate | 10 | 3 |
| Methyl thiophanate | 7 | 2 |
| Thiophanate | 10 | 3 |
| Thiophanate | 7 | 2 |
| A + Benomyl | 3 + 7 | 5 |
| A + Thiabendazole | 3 + 7 | 5 |
| A + Carbendazim | 3 + 7 | 5 |
| A + Fuberidazole | 3 + 7 | 5 |
| A + Methyl thiophanate | 3 + 7 | 5 |
| A + Thiophanate | 3 + 7 | 5 |
| B | 100 | 2 |

TEST EXAMPLE 2

Control effect on Powdery mildew of cucumber
(Preventive effect)

Sandy soil was packed in a plastic pot and cucumber (SAGAMI HANJIRO) was sowed and grown in a greenhouse for 20 days. The wettable powder of the test compound formulated according to Formulation Example 1 was diluted with water to a predetermined concentration and sprayed onto the leaves of a seedling of the cucumber which had developed a second leaf.

After sprayed, a spore-suspension of organisms causing Powdery mildew of cucumber was sprayed over the seedling of cucumber for inoculation. After inoculation, the seedling was grown at 20° C. for 10 days and then the control effect was examined. The results were shown in Table 2.

TABLE 2

| Test compound | Concentration of active ingredient applied (ppm) | Control effect |
| --- | --- | --- |
| A | 3 | 3 |
| A | 1 | 2 |
| Benomyl | 3 | 1 |
| Benomyl | 2 | 0 |
| Thiabendazol | 3 | 0 |
| Thiabendazol | 2 | 0 |
| Carbendazim | 3 | 1 |
| Carbendazim | 2 | 1 |
| Fuberidazole | 3 | 1 |
| Fuberidazole | 2 | 0 |
| Methyl thiophanate | 3 | 1 |
| Methyl thiophanate | 2 | 0 |
| Thiophanate | 3 | 1 |
| Thiophanate | 2 | 0 |
| A + Benomyl | 1 + 2 | 5 |
| A + Thiabendazole | 1 + 2 | 5 |
| A + Carbendazim | 1 + 2 | 5 |
| A + Fuberidazole | 1 + 2 | 5 |
| A + Methyl thiophanate | 1 + 2 | 5 |
| A + Thiophanate | 1 + 2 | 5 |
| B | 100 | 3 |

TEST EXAMPLE 3

Control effect on Blast of rice plant (Preventive effect)

Sandy soil was packed in a plastic pot and rice plant (KINKI No. 33) was sowed therein and grown in a greenhouse. A wettable powder of the test compounds formulated according to Formulation Example 1 was diluted with water to a predetermined concentration and sprayed onto the seedling of rice plant which had developed a third leaf.

After sprayed, a spore suspension of organisms causing rice blast was sprayed onto the seedling of the rice plant for inoculation. After inoculation, the rice plant was placed at 25° C. in a high humidity for 4 days and then the control effect was examined. The results were shown in Table 3.

TABLE 3

| Test compound | Concentration of active ingredient applied (ppm) | Control effect |
| --- | --- | --- |
| A | 75 | 3 |
| A | 25 | 1 |
| Benomyl | 75 | 3 |
| Benomyl | 50 | 2 |
| Thiabendazole | 75 | 2 |
| Thiabendazole | 50 | 1 |
| Carbendazim | 75 | 3 |
| Carbendazim | 50 | 2 |
| Fuberidazole | 75 | 3 |
| Fuberidazole | 50 | 2 |
| Methyl thiophanate | 75 | 3 |
| Methyl thiophanate | 50 | 2 |
| Thiophanate | 75 | 2 |
| Thiophanate | 50 | 2 |
| A + Benomyl | 25 + 50 | 5 |

TABLE 3-continued

| Test compound | Concentration of active ingredient applied (ppm) | Control effect |
| --- | --- | --- |
| A + Thiabendazole | 25 + 50 | 5 |
| A + Carbendazim | 25 + 50 | 5 |
| A + Fuberidazole | 25 + 50 | 5 |
| A + Methyl thiophanate | 25 + 50 | 5 |
| A + Thiophanate | 25 + 50 | 5 |

TEST EXAMPLE 4

Control effect on infection of Chinese cabbage (*Cercospollera brassicae*) (Curative effect)

Sandy soil was packed in a plastic pot and Chinese cabbage (Nagaoka No. 2) was sowed therein and grown in a greenhouse for 30 days. A spore suspension of Cercospollera brassicae of Chinese cabbage was sprayed to the seedling of the Chinese cabbage for inoculation which had developed second leaf. After inoculation, the seedling was placed at 20° C. in a high humidity for a day.

A wettable powder of the test compounds formulated according to Formulation Example 1 was diluted with water to a predetermined concentration and was sprayed onto the seedling so as to adhere to the leaves sufficiently. After sprayed, the seedling was grown in a greenhouse for 14 days and then the control effect was examined. The results were shown in Table 4.

TABLE 4

| Test compound | Concentration of active ingredient applied (ppm) | Control effect |
| --- | --- | --- |
| A | 10 | 3 |
| A | 3 | 1 |
| Benomyl | 10 | 2 |
| Benomyl | 7 | 2 |
| Thiabendazole | 10 | 2 |
| Thiabendazole | 7 | 1 |
| Carbendazim | 10 | 2 |
| Carbendazim | 7 | 2 |
| Fuberidazole | 10 | 2 |
| Fuberidazole | 7 | 1 |
| Methyl thiophanate | 10 | 2 |
| Methyl thiophanate | 7 | 1 |
| Thiophanate | 10 | 1 |
| Thiophanate | 7 | 1 |
| A + Benomyl | 3 + 7 | 5 |
| A + Thiabendazole | 3 + 7 | 5 |
| A + Carbendazim | 3 + 7 | 5 |
| A + Fuberidazole | 3 + 7 | 5 |
| A + Methyl thiophanate | 3 + 7 | 5 |
| A + Thiophanate | 3 + 7 | 5 |
| C | 100 | 0 |

What is claimed is:

1. A fungicidal composition which comprises an inert carrier and as an active ingredient (E)-1-(2,4-dichlorophenyl)-4,4-dimethyl-2-(1,2,4-triazol-1-yl)-1-penten-3-ol and methylbenzimidazol-2-yl carbamate in the ratio of 1 to 0.5-5 parts by weight in a total amount of 1 to 99% by weight.

2. A method for controlling fungi which comprises applying a fungicidally effective amount of the fungicidal composition according to claim 1, to said fungi.

* * * * *